United States Patent
Swenson et al.

(10) Patent No.: US 9,345,311 B2
(45) Date of Patent: May 24, 2016

(54) HANDS-FREE MEDICATION HOLDER HEADBAND AND METHOD OF USE

(71) Applicants: Daniel J Swenson, Randolph, NJ (US); Julie L Swenson, Randolph, NJ (US)

(72) Inventors: Daniel J Swenson, Randolph, NJ (US); Julie L Swenson, Randolph, NJ (US)

(*) Notice: Subject to any disclaimer, the term of this patent is extended or adjusted under 35 U.S.C. 154(b) by 0 days.

(21) Appl. No.: 14/656,281

(22) Filed: Mar. 12, 2015

(65) Prior Publication Data

US 2015/0289632 A1    Oct. 15, 2015

Related U.S. Application Data

(60) Provisional application No. 61/995,591, filed on Apr. 14, 2014.

(51) Int. Cl.
*A45F 5/00* (2006.01)
*A61M 5/31* (2006.01)
*A61F 17/00* (2006.01)
*A45C 11/00* (2006.01)

(52) U.S. Cl.
CPC . *A45F 5/00* (2013.01); *A61F 17/00* (2013.01); *A61M 5/31* (2013.01); *A45C 2011/007* (2013.01); *A45F 2200/0566* (2013.01)

(58) Field of Classification Search
CPC .............................. A45F 5/00; A61M 5/14244
USPC .......................................................... 224/18
See application file for complete search history.

(56) References Cited

U.S. PATENT DOCUMENTS

| | | | | |
|---|---|---|---|---|
| 4,174,793 A | * | 11/1979 | Wisowaty | A45C 11/32 224/240 |
| 4,970,631 A | * | 11/1990 | Marshall | A41D 20/00 362/105 |
| 5,053,932 A | | 10/1991 | Case | |
| 5,102,024 A | * | 4/1992 | Boersma | A42B 3/044 2/209.13 |
| 5,217,294 A | | 6/1993 | Liston | |
| 5,265,782 A | * | 11/1993 | McNamara | A41D 13/12 2/108 |
| 5,361,412 A | * | 11/1994 | Perry | A41D 13/0012 2/102 |
| 5,412,545 A | | 5/1995 | Rising | |
| 5,799,846 A | * | 9/1998 | Pfleger | A61M 5/1415 128/DIG. 6 |
| 5,893,496 A | * | 4/1999 | Katz | F21L 15/14 224/181 |
| 6,257,473 B1 | * | 7/2001 | Ringelstetter | E01H 1/1206 119/795 |
| 6,442,764 B1 | | 9/2002 | Badillo et al. | |
| 7,979,921 B2 | | 7/2011 | Cotutsca | |
| 8,108,944 B1 | | 2/2012 | Gilson, Sr. et al. | |
| 8,944,299 B2 | * | 2/2015 | Siew Kuang Choong | A61M 5/1411 224/148.2 |
| 2005/0279786 A1 | * | 12/2005 | Gac | A42B 1/24 224/181 |
| 2013/0327909 A1 | * | 12/2013 | Freelander | A45F 5/00 248/224.7 |

* cited by examiner

*Primary Examiner* — Brian D Nash
*Assistant Examiner* — Derek Battisti
(74) *Attorney, Agent, or Firm* — Thomas J. Germinario

(57) ABSTRACT

A headband can be used by medical doctors and animal technicians for a safe and efficient hands-free method of transporting filled, capped, medical syringes (without needle) and/or treatment items to treat patients, pastured cattle and livestock, and other pets, reducing risk of injury and stress to both technician and patients/animals, saving time, money, manpower, and medicinal product. The headband generally includes, the main elements—a headband strap to be fastened around the head that has heavy duty elastic gripping sleeves (loops) threaded onto it. Three of the sleeves are moveable along the strap, one is fixed (sewn) in place. These sleeves are used to hold various size syringes tightly to the headband to allow for hands-free work. The fixed sleeve has a seam, making it suitable to hold smaller 1-3 ml syringes.

2 Claims, 3 Drawing Sheets

HANDS-FREE MEDICATION HOLDER HEADBAND AND METHOD OF USE

REFERENCE TO RELATED APPLICATION

The present application claims the benefit of the filing date of U.S. provisional patent application No. 61/995,591, filed Apr. 14, 2014.

FIELD OF INVENTION

The present invention relates to the field of devices and methods for transporting holding, and/or deploying multiple items used in administering medication and/or veterinary/medical treatment to animals and/or humans (hereinafter referred to as "medication holder(s)"). More particularly, the present invention relates to a medication holder in the form of an adjustable headband used in a hands-free method of transporting, holding and deploying filled, capped medical syringes (without needles) and/or other veterinary/medical treatment supplies.

BACKGROUND OF THE INVENTION

In the process of administering medication and/or treatment, it is often advantageous for a practitioner/technician to have his/her hands free, without the necessity of manually holding onto syringes, tubes and/or other treatment supplies or instruments before such items need to be used. This is particularly true when administering medication and/or treatment to animals, such as livestock, which require restraint in preparation for medication/treatment. In some circumstances for certain human patients as well, use of a hands-free medication holder may be beneficial and appropriate.

Therefore, it is advantageous for a veterinary or medical practitioner or technician to have a hands-free means of safely transporting and retaining on his/her person medication and/or treatment supplies. It is particularly advantageous to provide such hands-free means for transporting and holding filled and capped medical syringes, so that the practitioner/technician can focus his/her full attention on handling an animal or unruly patient without fear of dropping or breaking a syringe, or having its plunger engaged and medicine released unexpectedly.

It is also advantageous to provide for hands-free transport and temporary storage of medication and/or treatment items in a location on the person of the practitioner/technician which is "out of harm's way," in the sense of being least likely to sustain an impact in the course of restraining an animal or an unruly patient. The safest location tends to be the head of the practitioner/technician, who is typically trained and learns from experience to keep his/her head a safe distance from contact with a frightened animal or patient.

Consequently, it is advantageous to provide a wearable head-band capable of securely retaining multiple medication/treatment items in a manner that such items remain readily accessible and quickly removable by a practitioner/technician in the course of administering medication or treatment to an animal or human patient. This and other useful objectives are addressed by the present invention, as further described herein.

SUMMARY OF THE INVENTION

The invention generally relates to a medication holder headband which includes the main elements of the invention—a headband strap along with heavy duty elastic gripping sleeves (loops) threaded onto it. Some of the sleeves are non-fixed, able to slide along the strap, some are fixed (sewn) in place. These sleeves are used to hold various size syringes tightly to the headband to allow for hands-free work. The fixed sleeve has a seam, making it suitable to hold smaller items, such as 1-3 ml syringes.

There has thus been outlined, rather broadly, some of the features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The purpose of the invention is to provide medical doctors and animal technicians with a headband used for a safe and efficient hands-free method of transporting filled, capped, medical syringes (without needle) to treat patients, pastured cattle and livestock, and other pets, reducing risk of injury and stress to both technician and patients/animals, while saving time, money, manpower, and medicinal product.

Another object is to provide a headband that allows for safe hands-free method to transport filled, capped syringe(s) to the location of the patient/animal(s) to be treated.

Another object is to provide a headband that provides for the technician to have full attention of handling patient/animal without worry of dropping syringe, having syringe break or having plunger released due to unexpected force during restraint of patient/animal (i.e. technician transporting syringe in shirt, pant, vest, or jacket pocket and is kicked or struck by patient/animal during restraint as they are prepped to be treated).

Another object is to provide a headband that reduces the risk of injury to technician by placing the syringe in a location (on the headband around the head) that is unlikely to sustain force in the process of restraining the animal (or patient) in preparation for treatment. Technicians typically are trained and learn from experience, to keep their head a safe distance from contact with frightened and/or aggressive animal.

Another object is to provide a headband that reduces risk to animals by preventing loss of medicinal product filled syringe, dropped in a field, that could be stepped on or accidentally ingested by a healthy animal. (i.e. product dropped during physical restraining process, lost, and then consumed by a young animal at a dose that is dangerous for his/her size, age, or an animal that this medication was not intended for).

Another object is to provide a headband that saves money by reducing loss of medicinal product. (As can happen when syringe is carried on the body, and product is expectedly emptied into pocket due to force during restraint.)

Another object is to provide a headband that saves time and manpower by providing easy and quick access to syringe.

Another object is to provide a headband that reduces stress level of technician and patients/animals by reducing treatment/handling time and the number of technicians needed for handling.

Other objects and advantages of the present invention will become obvious to the reader and it is intended that these objects and advantages are within the scope of the present invention. To the accomplishment of the above and related objects, this invention may be embodied in the form illustrated in the accompanying drawings, attention being called to the fact, however, that the drawings are illustrative only, and that changes may be made in the specific construction illustrated and described within the scope of this application.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENT

A. Overview

Figure 1:
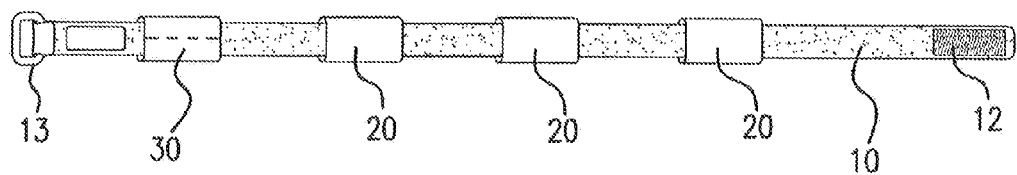
FIG. 1: is a plan view of the present invention, showing the three main elements: the headband strap 10 with loop side facing up; the non-fixed elastic gripping sleeves 20 along the band; and fixed elastic gripping sleeve 30, sewn in place. The sub-elements: the patch of hook-and-loop material on the end of the strap 12; and the D-ring 13 are also shown in this view.
Figure 2:
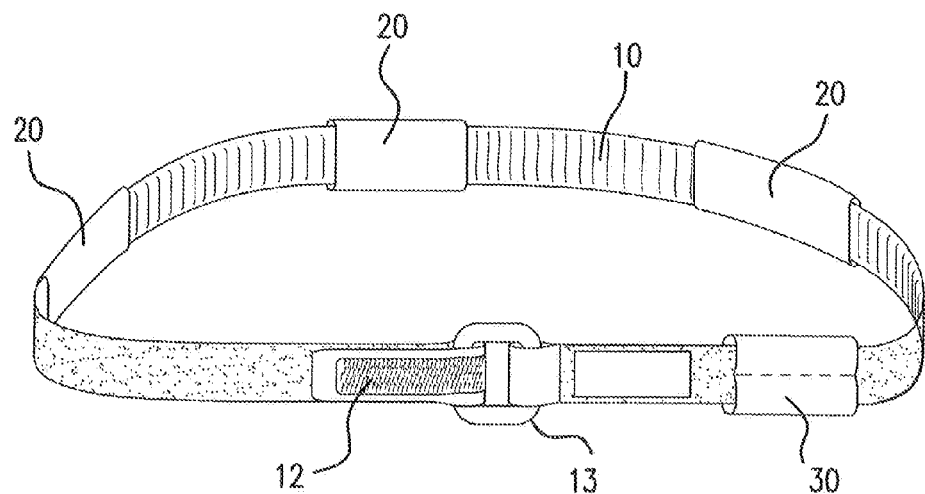
FIG. 2: is a front perspective view of the headband, as it would look strapped in place around a user's head. In this figure both the outside surface of the headband strap 10, the loop side, and the inside, elastic side of the headband strap 10 are in view. The elastic gripping sleeves are shown 20 and 30 in this figure. The D-ring 13 is shown in use with the headband strap 10 threaded through it and secured in place on the headband strap by use of the patch of hook material 12.

Turning now descriptively to the drawings, in which similar reference characters denote similar elements throughout the several views, the figures illustrate the main elements of the invention which are a headband strap 10, along with heavy duty elastic gripping sleeves 20 30 (loops) threaded onto it. Three of the sleeves are moveable 20 along the strap, the forth is fixed 30 (sewn) in place. These sleeves are used to hold various size syringes 40 tightly to the headband to allow for hands-free work. The fixed sleeve 30 has a seam, making it suitable to hold smaller 1-3 ml syringes 41.

In designing the headband and determining materials, sizes, structure and operation of the invention, several variations were tested. The descriptions to follow, of the main elements and sub-elements, are those that met the best mode contemplated by the inventor.

B. Headband Strap

Figure 4:
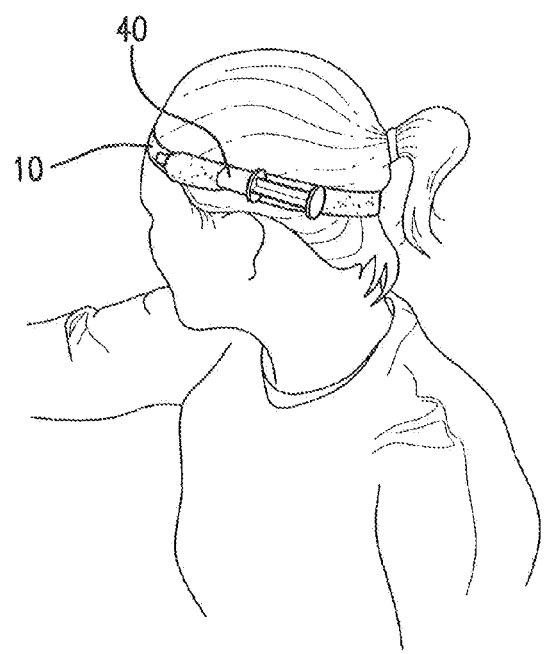
FIG. 4: is a schematic view of the headband worn by a veterinarian, directly on the head (not over a hat), preparing for treatment of a heifer through a chute. It shows placement of a syringe 40 in a non-fixed gripping sleeve 20 that has been moved in place for a left-handed user.

The first main element of the present invention is the elastic headband strap 10, which is made of polyester and nylon in a strap form that is 25 mm wide×680 mm long. The material is a soft elastic with a suede like texture on one side and textured loop material on the other. On the last 50 mm from the end of the headband strap 10, on the loop side, there is a piece of hook material 12 sew on top, over the length and width of the headband strap 10, hook side out, measuring 25 mm×50 mm. The other end of the headband strap 10 has been threaded through a 20 mm×35 mm plastic D-ring 13, folded over at 25 mm and then sewn on to the headband strap 10 to secure the D-ring 13 to the end of the headband strap 10. (See FIG. 1) The headband is to be used by placing the smooth sueded side of the elastic headband 10 against the user's head, or fitted over the user's cap or hat. The strap is then wrapped horizontally, across the user's forehead, just above the ears, and secured at the back of the head, as the end is threaded through the D-ring 13. The elastic headband strap 10 is pulled to fit snuggly around the head and then the end of the headband strap's hook side 12 pressed firmly to the loop side of the headband strap to secure in place. (See FIG. 4)

Figure 3:
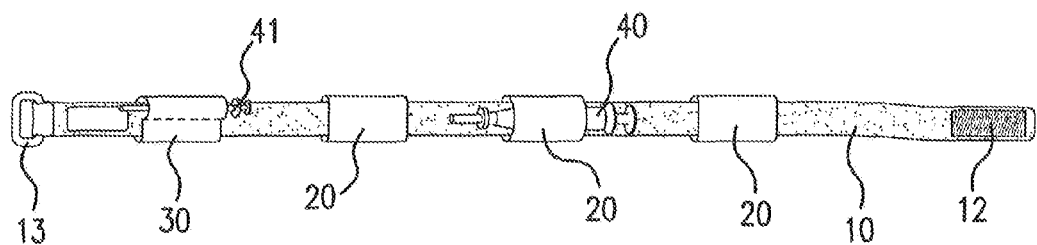
FIG. 3: is an operational plan view of the present invention, illustrating the headband with two syringes 40 41 secured in the sleeves on the band. Here, one syringe 40 is being held in place by a non-fixed elastic gripping sleeve 20 that the user has slid into place for easy access. The fixed elastic gripping sleeve 30 is also in use, holding a 1 ml syringe 41 securely in place.

The function of the elastic headband strap 10 is to provide the device (structure) to thread the heavy duty waistband elastic gripping sleeves made of polyester and nylon elastic (20 and 30) onto. The elastic headband strap 10 provides for three fitted non-fixed elastic gripping sleeves 20 to be free sliding on the headband 10 to hold loaded, capped medical syringes (without needle), and/or other implements in various locations tightly along the headband 10. On the headband strap 10, there is an additional, identical elastic gripping flat sleeve 30 that is fixed in place. It is 50 mm wide and has been threaded onto the headband strap 10 50 mm from the D-ring 13 seam to 100 mm, and then sewn in place with heavy duty core-spun polyester thread, with a securing seam that runs the width of the sleeve, parallel to the top edge of the headband strap. This fixed position sleeve on the headband strap, allows for a snug fit for smaller syringes. (See FIG. 3).

In testing the headband, several structural variations were tried, including using various lengths and widths of elastic hook and loop strap. The widths, 38 mm and 50 mm of elastic hook and loop headband strap was tested. These widths tested to be too wide for functional use and tended to pucker along the head and also the hat and did not fit needs of best mode of operation. It was found that the 25 mm width, and the 680 mm length of elastic headband strap 10 of would work for all standard adult head sizes from hat sizes small (54 cm) through size XXL (63.5 cm). This allows for headband to be a "one size fits most" product, rather than having to make different sizes.

Various materials could also be used successfully in place of the elastic hook and loop headband strap 10, including using a neoprene material strap with hook and loop material just on the ends. This material would work well initially, but would not wear well over time. In the testing, the neoprene model faded, and wore out quickly. The headband strap 10 was also made using leather and a belt buckle type of closure in place of the D-ring 13. This option was heavy on the head. The headband was also made using Kevlar mesh tape in the lining of the elastic hook and loop material headband strap 10 to make the band impenetrable. This option became costly to produce and proved unnecessary. The product was tested over and over without the Kevlar, without the needle in place during transportation, and the product without the Kevlar tape showed significant savings of time and medicinal product, and reduction of stress levels and use of manpower. It was determined the transportation of syringe with needle attached was not necessary for best mode of use, for safety, function, and savings.

Various closures can be used effectively on the headband. The headband strap 10 can also be made from a hook and loop material 12, or other elastic or neoprene material that does not use a D-ring 13 on the end, and instead just has hook and loop closure, snap, button and elastic loop or button hole, or other fastener. This design was tested, and found that the hook and loop closure, without the D-ring, did not hold with weight of syringes as well as the strap with the D-ring 13. The headband with the D-ring held the elastic hook and loop headband 10 more secure when weighted with syringes.

Alternatively, the headband 10 could be omitted, and the sleeves (20 and 30) could simply be sewn directly onto a hat or cap. The headband 10 design was preferred, as it provides for wear with or without a hat and can fit on hats for different weather conditions if used outdoors. Sewing the sleeves directly onto a hat greatly reduces the flexibility of use, since it eliminates the ability to move loops and treatment items along the headband.

C. Elastic Gripping Sleeve—not Fixed Location

Figure 5:
FIG. 5: is a schematic view showing the headband worn by a farmer, over his hat, during treatment of a calf in the field. It shows placement of a syringe 40 in a non-fixed gripping sleeve 20 by a right-handed user.

The second main element is three identical 50 mm wide sleeves (loops) of elastic that are threaded through the elastic headband strap 10. These elastic gripping sleeves 20 are made from heavy stretch waistband elastic, folded in half and sewn together with heavy duty core spun polyester thread from the fold to create a (loop) sleeve. The sleeves are then turned right side out and threaded onto the elastic headband strap. These three elastic gripping sleeves 20 slide freely along the headband strap 10, and can be positioned where needed. (See FIG. 1) The function of these gripping sleeves 20 is to hold syringes 40 and/or implements snugly to the band 10 along the head, allowing physician/technician to have free hands. A loaded, capped medical syringe 40 can be easily slid through the elastic gripping sleeve 20 with one hand. The syringe 40 is positioned through the sleeve 20 so that the syringe is approximately centered through the sleeve 20 from top to bottom and side to side of the sleeve. (See FIGS. 3, 4 and 5) In this position, the syringe is held snuggly between the loop side of the elastic headband 10 and the inside of the sleeve 20, along the user's head. The purpose of having the sleeves 20 free to slide on the elastic headband strap 10 is to allow for various options of spacing syringes depending on size and length of the syringe 40, and location needed. One or all sleeves (20 and 30) can be used at once, depending on the size of the syringes being used, and the weight of the product in the syringes. Flexible spacing also allows for both right-handed users and left-handed users to position sleeves 20 where they are most accessible for their reach. It also provides for movement of sleeves 20 depending on the size of the user's head/hat. User's with small head size will have less space along the band to slide the sleeves, while user's with larger heads will have more sleeve placement flexibility.

Other structural variations could include various widths of elastic sleeve 20. When tested, a sleeve with a narrower width than 50 mm did not secure the syringes firmly in place during action. Wider sleeves made it more difficult to get the syringes in and out of the sleeves.

Rather than non-fixed sleeves that could be moved along the headband strap, fixed sleeves were tested. Using all "fixed in place" sleeves made for less flexible use of the size and number of syringes. Best mode of design during testing was having three non-fixed 50 mm wide elastic gripping sleeves 20 and one elastic gripping sleeve in a fixed location 30.

D. Elastic Gripping Sleeve—Fixed Location

This fixed elastic gripping sleeve 30 is the same size and structure and materials as the second element, the non-fixed elastic gripping sleeve 20. The difference is, that after being threaded onto the elastic headband strap 10, it is sewn into place on the headband strap 10 at 50 mm from the D-ring seam to 100 mm. (See FIG. 1) The securing seam runs lengthwise, parallel to the top edge of the sleeve, through the sleeve 30 and headband strap 10 10 mm from top edge of the sleeve 30. This fixed position sleeve 30 on the headband strap 10, allows for a snug fit for smaller syringes of 1-3 ml. (See FIG. 3)

Structurally, the fixed sleeve 30 can be sewn equal distance from the top and bottom edge of strap, but this makes both the top and bottom section of the sleeve too tight to hold a 3 ml syringe. Alternatively, more or fewer sleeves can be used and the sleeves can all be fixed or all slide free or any combination of some fixed and some sliding. The sleeves can be of various widths as well, but 50 mm tested well for holding syringes secure in action.

E. Connections of Main Elements and Sub-Elements of Invention

The three main elements and four sub-elements are connected in structure and operation. The main element of the headband is the elastic headband strap 10 that provides the device/structure for the second and third elements, the non-fixed 20 and the fixed 30 elastic gripping sleeves. (See FIG. 1)

Two sub-elements, the 50 mm wide, heavy duty waistband elastic 21 and heavy duty core-spun polyester thread are used to form (sew) elastic loops which are threaded onto the headband strap 10 and become the gripping sleeves (20 & 30). Three of the sleeves 20 remain moveable along the headband strap 10 and are used to hold various size syringes and implements snuggly against the headband and head, allowing user to keep hands free. (See FIG. 4 and FIG. 5) One of the sleeves 30 is sewn into place on the headband strap 10 at 50 mm from the D-ring seam to 100 mm. This seam runs parallel to the top edge of the headband strap 10, securing the sleeve 30 in a fixed position on the headband strap 10. This allows for a snug fit for smaller syringes of 1-3 ml. 41. (See FIG. 3)

Two other sub-elements, the patch of hook material 12 and a plastic D-ring 13, are attached (sewn on) opposite ends of the length of headband strap 10 to provide for a method of securing the headband strap 10 securely to the head. In use, this end hook patch end 12 is threaded through the D-ring 13 and folded back to secure the end with hook patch material 12 to the loop material side of the headband strap 10. (See FIGS. 3, 4 and 5)

F. Operation of Preferred Embodiment

To utilize the headband, a user wears the elastic headband 10 horizontally around user's head (or around the outside of a hat on user's head) with the sueded elastic side in, against the head/hat. The loop material side is facing out. The center of the length of the headband 10 is placed approximately at the center of the forehead. The headband 10 is wrapped around the head just above the ears, with the D-ring 13 centered at the back of the head. The patch of hook material 12 at the end of the headband 10 is threaded through underside of the D-ring 13 and pulled gently up, away from the head, to feel the headband 10 comfortably tightened around the head. The patch of hook material 12 the end of the headband 10 is folded over the D-ring 13 and pressed firmly in place, attaching to the loopside of the headband 10 to hold the headband in place. (See FIG. 4 and FIG. 5)

The three non-fixed elastic gripping sleeves 20 on the headband, are then maneuvered along the headband 10 to the location that works best for the number and size of the syringes or implements to be held by the elastic gripping sleeves 20. Once the sleeves 20 are in the position desired, a loaded syringe can be fitted into each of the sleeves 20 by placing the tip of the capped syringe just under the elastic sleeve 20 and sliding it into the sleeve (between the sleeve and the headband 10) until it is centered in the sleeve 20. When using small syringes of only 1-2 ml, or small implements, the fixed elastic sleeve 30 is utilized as it is a tighter fit, designed for this purpose.

For right-handed users, who plan to utilize the fixed gripping sleeve 30, the headband 10 is placed on the head so that the hook end 12 threads under the D-ring 13 and is fastened to the left. (The fixed gripping sleeve 30 is then on the right side for easy reach.) For left-handed users, utilizing the fixed gripping sleeve 30, the headband 10 is flipped around so that the hook end 12 is threaded under the D-ring 13 and fastened to the right side, (so that the fixed sleeve 30 is then on the left side for easy reach).

For both right and left handed users, who are utilizing only the moveable sleeves 20, the headband 10 can be fastened to the right side or left side and elastic gripping sleeves 20 can be moved into position as needed and most convenient for their reach. (See FIG. 4 and FIG. 5)

Once the headband 10 is comfortably in place on the head/ or hat, and the syringes 40 or implements are in place, user is ready to perform needed treatment or task. (See FIG. 4 and FIG. 5) When user is ready, with one hand, they simply slide the syringe 40 forward, out from the elastic gripping sleeve 20, uncap the syringe 40, and treat. Or, they attach a needle if one is needed. (Some syringes are filled with oral solutions or pastes, or topical ointments that don't require a needle.)

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention in which all terms are meant in their broadest, reasonable sense unless otherwise indicated. Any headings utilized within the description are for convenience only and have no legal or limiting effect.

Although the preferred embodiment of the present invention has been disclosed for illustrative purposes, those skilled in the art will appreciate that many additions, modifications and substitutions are possible, without departing from the scope and spirit of the present invention as defined by the accompanying claims.

What is claimed is:

1. A hands-free method for accessibly retaining, on a head or a head covering of a user, one or more medication items to be used in administering treatment to an animal or human subject, the method comprising the following steps:
   (a) providing a headband, comprising a strip of elastic material, having a length, two ends, a front side, and a reverse side, and having a conjugate pair of closure means at either end of the strip;
   (b1) providing one or more moveable gripping sleeves, each comprising a deformable tubular loop of elastic material, shorter than the length of the headband;
   (b2) providing one or more fixed gripping sleeves, each comprising a deformable tubular loop of elastic material, shorter than the length of the headband;
   (c1) threading the headband through each of the moveable gripping sleeves, so that each of the moveable gripping sleeves wraps around a portion of the headband without being attached to either side of the headband;
   (c2) threading the headband through each of the fixed gripping sleeves, so that each of the fixed gripping sleeves wraps around a portion of the headband, and attaching each of the fixed gripping sleeves to the front of the headband by a longitudinal sleeve seam, so as to divide the loop lengthwise into two horizontal sleeve channels;
   (d) placing the headband around the head or head covering of the user, and coupling the closure means together, so as to enclose the headband elastically around the head or head covering of the user;
   (e) sliding each of the moveable gripping sleeves along the length of the headband to one of multiple sleeve positions along the headband;
   (f1) inserting and retaining one or more first treatment items between one of the moveable gripping sleeves and the front side of the headband;
   (f2) inserting and retaining one or more second treatment items in one or more of the sleeve channels of one of the fixed gripping sleeves;
   (g1) preparing the subject for treatment while the first treatment items are retained in the moveable gripping sleeves on the headband; and
   (g2) preparing the subject for treatment while the second treatment items are retained in the fixed gripping sleeves on the headband;
   (h1) accessing the first treatment items, while administering treatment to the subject, by removing some or all of the first treatment items from the moveable gripping sleeves on the headband; and
   (h2) accessing the second treatment items, while administering treatment to the subject, by removing some or all of the second treatment items from the fixed gripping sleeves on the headband.

2. The method of claim 1, further comprising in step (a), providing the closure means comprising a D-ring at one end of the headband and a hook-and-loop fastener at the other end of the headband, and further comprising in step (d), inserting the hook-and-loop fastener through the D-ring, and then adhesively doubling over the hook-and-loop fastener, so as to enclose the headband elastically around the head or head covering of the user.

* * * * *